(12) United States Patent
Schneider

(10) Patent No.: US 10,188,486 B2
(45) Date of Patent: Jan. 29, 2019

(54) DENTAL IMPRESSION, DRILLING TEMPLATE AND METHOD FOR PROVIDING A RELATIVE LOCATION FOR CREATING A DRILLING TEMPLATE

(75) Inventor: Sascha Schneider, Mühltal (DE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 13/983,520

(22) PCT Filed: Feb. 2, 2012

(86) PCT No.: PCT/EP2012/051728
§ 371 (c)(1),
(2), (4) Date: Aug. 2, 2013

(87) PCT Pub. No.: WO2012/104364
PCT Pub. Date: Aug. 9, 2012

(65) Prior Publication Data
US 2013/0302752 A1    Nov. 14, 2013

(30) Foreign Application Priority Data
Feb. 3, 2011 (DE) .......................... 10 2011 003 561

(51) Int. Cl.
*A61C 8/00* (2006.01)
*A61C 1/08* (2006.01)
(Continued)

(52) U.S. Cl.
CPC .......... *A61C 8/0001* (2013.01); *A61B 17/176* (2013.01); *A61C 1/084* (2013.01);
(Continued)

(58) Field of Classification Search
CPC .......... A61C 1/082; A61C 1/084; A61C 1/085; A61C 8/001; A61C 8/0089; A61C 8/009; A61C 19/04; A61C 19/055
(Continued)

(56) References Cited

U.S. PATENT DOCUMENTS 5,076,785 A * 12/1991 Tsai ..................... A61C 9/0006
                                                   433/46
6,319,006 B1   11/2001 Scherer et al. ............... 433/214
(Continued)

FOREIGN PATENT DOCUMENTS

DE    199 52 962 A1    5/2001
DE    102 00 505 A1    7/2003
(Continued)

OTHER PUBLICATIONS

Dec. 26, 2017 Office Action in Japanese Patent Application No. 2017-018381 (with English translation).

*Primary Examiner* — Ralph Lewis
(74) *Attorney, Agent, or Firm* — Dentsply Sirona Inc.

(57) ABSTRACT

A dental impression that includes an underside and a connecting part. The underside has a negative form of at least one partial area of a jaw and at least one implant site located in the partial area of the jaw. The connecting part is a recess arranged on an upper surface of the dental impression opposite the underside in the area of the negative form of the implant site, and has a longitudinal axis defined along a depth direction of the recess. The recess has a geometry that is rotationally asymmetric about the longitudinal axis, and an external contour of the connecting part is asymmetrical in a plane perpendicular to the longitudinal axis of the connecting part. The connecting part has a lowered base as a depth stop, the lowered base being within the recess and below the upper surface of the dental impression.

15 Claims, 4 Drawing Sheets

(51) Int. Cl.
*A61B 17/17* (2006.01)
*A61C 13/00* (2006.01)
*A61B 17/56* (2006.01)

(52) U.S. Cl.
CPC ........ *A61C 8/009* (2013.01); *A61B 2017/568* (2013.01); *A61C 13/0004* (2013.01)

(58) Field of Classification Search
USPC ............ 433/34, 37, 72, 74, 75, 76, 173, 214
See application file for complete search history.

(56) References Cited

U.S. PATENT DOCUMENTS

| | | | |
|---|---|---|---|
| 6,468,078 B2* | 10/2002 | Guillaume et al. | 433/45 |
| 6,969,256 B2* | 11/2005 | Sethi et al. | 433/173 |
| 7,845,943 B2* | 12/2010 | Meitner | A61C 1/084 |
| | | | 433/75 |
| 7,905,726 B2 | 3/2011 | Stumpel | 433/75 |
| 2002/0137003 A1* | 9/2002 | Knapp | A61C 1/084 |
| | | | 433/76 |
| 2002/0177104 A1* | 11/2002 | Klein et al. | 433/173 |
| 2007/0154862 A1* | 7/2007 | Kim | A61C 1/084 |
| | | | 433/72 |
| 2009/0136902 A1* | 5/2009 | Zundorf et al. | 433/223 |
| 2010/0003635 A1 | 1/2010 | Feith | |
| 2010/0124731 A1* | 5/2010 | Groscurth et al. | 433/213 |
| 2010/0185201 A1* | 7/2010 | Kim | A61C 1/12 |
| | | | 606/80 |
| 2010/0233647 A1 | 9/2010 | Yang | 433/66 |
| 2010/0297574 A1* | 11/2010 | Llop | A61C 1/084 |
| | | | 433/75 |
| 2011/0008751 A1 | 1/2011 | Pettersson | |
| 2011/0159455 A1 | 6/2011 | Stumpel | 433/60 |
| 2012/0053593 A1 | 3/2012 | Abboud | 606/96 |

FOREIGN PATENT DOCUMENTS

| | | |
|---|---|---|
| DE | 10 2005 023 028 A1 | 11/2006 |
| DE | 10 2005 040 739 A1 | 3/2007 |
| DE | 20 2007 005 595 U1 | 11/2007 |
| DE | 10 2007 034 343 A1 | 1/2009 |
| EP | 1 502 556 A2 | 7/2004 |
| EP | 1 502 556 | 2/2005 |
| EP | 2 228 029 A2 | 9/2010 |
| JP | 2007-512079 A | 5/2007 |
| JP | 2008-523935 A | 7/2008 |
| WO | 99/32045 A1 | 7/1999 |
| WO | 2007/129955 A1 | 11/2007 |
| WO | 2008/045965 A2 | 4/2008 |
| WO | 2010/097405 A1 | 9/2010 |
| WO | 2011/087794 A1 | 7/2011 |

* cited by examiner

DENTAL IMPRESSION, DRILLING TEMPLATE AND METHOD FOR PROVIDING A RELATIVE LOCATION FOR CREATING A DRILLING TEMPLATE

CROSS REFERENCE TO RELATED APPLICATION

The present application is a national-stage entry under 35 U.S.C. § 371 of International Application No. PCT/EP2012/051728 filed on Feb. 2, 2012, and claims the benefit of foreign priority under 35 U.S.C. § 119 of German Application No. 10 2011 003 561.3 filed on Feb. 3, 2011. Each of those applications is incorporated herein in its entirety, as if set forth fully herein.

TECHNICAL FIELD

The invention relates to a dental impression, a drilling template and a method for providing a relative location between an implant site in a jaw and a 3-D measurement dataset for the implantation site and a method for creating a drill guide.

PRIOR ART

A number of drilling templates are known from the prior art, which enable the controlled performance of planned drilling for implants. Using these types of drilling template, it can be ensured that a targeted drilled hole has a calculated drilling route, a calculated drilling depth and a calculated drilling diameter.

DE 199 52 962 A1 discloses a method for creating a drill guide for a dental implant, wherein an X-ray of the jaw is first taken and a three-dimensional visual measurement of the visible surface of the jaw and the teeth is then made. The measurement datasets from the X-ray image and the three-dimensional visual recording are correlated with one another. By reference to the information available, such as the type and the location of the implant relative to the adjacent teeth, a template is designed and created, which is supported on the adjacent teeth and thus, precise drilling of the implant guide hole is enabled. By reference to the X-ray data, the implant can be specified and positioned in the established fashion. By reference to information gained concerning the surface structure, i.e. the occlusal surfaces of adjacent teeth, an implant guide can be ground in the form of a drilling template by means of a CAD/CAM unit. By reference to the measurement data, a CAD/CAM device is in a position to produce the drilling template and a drill guide for the drill using the negative of the occlusal surfaces. An end stop is positioned on the drilling template, which determines the drilling depth.

A method for producing a drill guide for implants is known from WO 99/32045, wherein a three-dimensional computer image is generated using an image of the jaw with reference to a dental impression surface, the position and the drilling depths of the drilled holes are determined and a set of implant hole coordinates is entered in a computer-controlled production machine. By means of a precision tool, a drill guide socket is prepared for each of the sets of coordinates for the drilled holes entered beforehand in a position corresponding with the position and orientation of the drilled holes determined by reference to the section of the jaw.

One disadvantage of this method is in that the majority of CAD/CAM machines have a restricted degree of freedom and hence the drilling templates can only be produced in accordance with the known method and by means of this type of CAD/CAM machine for a limited range of indications. For this reason, in most cases, the drilling template is either produced individually in the laboratory or centrally, after prior CAD/CAM planning, using a hexapod, for example, the design of which allows a flexibility of the object to be processed in all six degrees of freedom, and vertical drilled holes are placed by means of a parallelometer. Generally, CT-DVT templates, bite plates and plaster models of the jaw are used in the central production. These are assembled on the elaborately designed hexapod and are adjusted with the aid of multiple measuring points. This process is very elaborate and hence also prone to error.

The object of this invention is to provide a method that enables the production of a drilling template in as simple and rapid a fashion as possible, using a conventional production machine with limited degrees of freedom.

DESCRIPTION OF THE INVENTION

One subject matter of the invention is a dental impression comprising a negative form on an underside of at least one partial area of a jaw and at least one implant site located in this partial area of the jaw. The dental impression may, at least partially, consist of a radiolucent material and/or a material that is as little visible as possible in an MRI image. On an upper surface opposite the underside of the dental impression, the dental impression has a connecting part in the area of the negative form of the implant site that is formed opposite the upper surface of the dental impression as a rise and/or a recess. This rise and/or recess has a longitudinal axis in the direction of its elevation or depression opposite the upper surface of the dental impression. The rise and/or recess has a geometry that, in terms of rotational geometry, distinctly rotates about the longitudinal axis.

A dental impression is a negative cast of a jaw or of a part of a jaw, that is, a cast of the entire jaw or a partial cast of the jaw. Hence, the dental impression has an underside with the negative form of the jaw or a part of the jaw and an upper surface opposite the underside. Initially, a soft, malleable material, referred to, for example, as modeling compound, is used, which later hardens. While malleable, this is applied onto the jaw or the part of the jaw, such that the shape of the jaw or of the teeth located on the jaw is reproduced in the malleable material as a negative. The material is cured in this location. In its hardened condition, the dental impression has a completely solid, not deformable shape or at least a shape that always returns to its original shape when it is deformed.

The dental impression according to the invention is characterized, for example, in that it is designed from radiolucent material. Due to its radiolucency, a dental impression according to the invention is not visible in an X-ray image. Thus, an X-ray image can be taken of a patient's jaw with a dental impression according to the invention positioned on the jaw, without the dental impression obscuring parts of the jaw and/or the teeth still in place on the X-ray image.

In order to obtain a corresponding effect for an MRI exposure, an insulating material can be used, which, as a rule, is not visible or is inconspicuous in an MRI image, for example, polyurethane, polyethylene, polymers or fiberglass. All materials, which only generate the smallest number of signals possible in an MRI image and, in particular, which do not obscure the signals generated by bones or teeth, are suitable. In particular, this type of material should have a significantly lower density than the density of the surrounding tissues, such as the jawbone, the teeth and the surrounding soft tissue.

The dental impression according to the invention spans an implant site and at least one region immediately adjacent to the implant site, e.g. adjacent teeth, such that, for example, the dental impression removed from the jaw can be replaced precisely and easily by reference to adjacent teeth.

Connecting part denotes an area of the dental impression which is characterized by a geometry enabling a further component to be mounted on the upper surface of the dental impression. Here, for example, this can be a recess, in which a further component can be at least partially inserted. The connecting part can also be designed as an elevation, on which a further component can be positioned.

The molding of the connecting part is characterized according to the invention in that it has a longitudinal axis that proceeds in the direction of the elevation or depression of the connecting part relative to the surface of the dental impression and that the external contour of the connecting part is asymmetrical in a plane perpendicular to this longitudinal axis. This type of asymmetry in the direction of rotation around the longitudinal axis ensures a precise placement of a further component in respect of its rotation around the longitudinal axis with a geometry suitable for the placement.

Advantageously, the dental impression can be designed as a single piece with the connecting part. This may be a particularly simple production variant for providing a dental impression according to the invention.

Advantageously, a separate component can be available that comprises a connecting part corresponding at least partially with a negative of the connecting part of the dental impression and that can be introduced at least partially into the connecting part of the dental impression or can be positioned on the connecting part.

The connecting part of the dental impression enables a further component to be arranged easily and precisely on the dental impression, for example, by inserting or positioning, for which the additional component also has a connecting part. The connecting part of the separate component is a area or part of the component, which is suitable for attaching or connecting the separate component to the dental impression. For this purpose, the connecting part of the component, for example, has the negative form of the connecting part of the dental impression, such that it can be interlocked therewith. The connecting part of the separate component may also only partially correspond with the negative form of the connecting part of the dental impression, wherein only a partial interlock is achieved.

Advantageously, the component can be designed as a single-piece or as a multi-piece positioning aid, consisting at least partially of a material which is radiopaque and/or visible in an MRI image.

A positioning aid according to the invention is a component that, in contrast with the dental impression, is at least partially visible in an X-ray image or an MRI image. For an X-ray image, the positioning aid consists at least partly of radiopaque material. In respect of MRI images, a material is suitable, for example, that has a density or spin lattice relaxation rates clearly distinguishable from those of the jawbone, the teeth and the surrounding soft tissues. Conductive materials such as certain metals, for example, are suitable.

Advantageously, the rise or recess of the connecting part has at least one side panel adjacent to the upper surface of the dental impression. This type of side panel is particularly suitable for retaining further components by interlocking.

Advantageously, the recess of the connecting part has a lowered base opposite the upper surface of the dental impression or the rise of the connecting part has a raised cap opposite the upper surface of the dental impression. Using the base or the cap of the connecting part of the dental impression as a depth-stop, the location in the direction of the rise or recess of a component to be mounted can be determined. This can be effected, for example, by inserting the component to be mounted until a component surface suitable for this comes into contact with the base or by inserting the cap into the connecting part of the dental impression or by attaching the connecting part of the dental impression.

In addition, the invention relates to a drilling template for a drilled hole to be carried out at an implant site, which consists of a dental impression according to the invention and at least one drill guide for guiding a drill. The drill guide has a connecting part for connecting with the dental impression, which at least partially corresponds with a negative of the connecting part of the dental impression. The drill guide also has an access opening, which determines a drilling route relative to the connecting part.

Easy assembly of the drill guide and the dental impression in a definitive location can be ensured by the respective connecting part of the dental impression and the drill guide.

Thus, it can also be ensured that the access opening of the drill guide proceeds in a predetermined direction, namely a desired drilling direction, relative to the dental impression and hence, where the dental impression is arranged on the jaw, also relative to the jaw.

Advantageously, at least the connecting part of the drill guide can be produced by milling or grinding. This is a particularly simple production method. In terms of processing directions, however, conventional milling and grinding machines only have a limited number of degrees of freedom. Hence, the drill guide according to the invention is designed in such a way that it can also be produced using a conventional milling or grinding machine with limited degrees of freedom.

Advantageously, the drill guide has a support surface for support on the upper surface of the dental impression. This is one further option for controlling the location of the drill guide arranged on the dental impression. This type of support surface can constitute a depth stop, for example, for a drill guide able to be inserted into a connecting part of a dental impression formed as a recess or for a drill guide able to be attached onto a connecting part of a dental impression designed as an elevation, and hence can determine the location, at least in terms of a direction proceeding in the direction of the elevation or recess.

Advantageously, the access opening of the drill guide is designed as a cylinder and has a diameter that corresponds with a defined drill diameter.

By this means, the opening of the drill guide, particularly when mounted on the dental impression, can be used to guide a drill.

Advantageously, the drill guide comprises at least one adapter, wherein the adapter has a cylindrical access opening with a diameter corresponding with a defined drill diameter, and an external geometry with an interlocking area at least partially in the access opening of the drill guide and a terminal area connecting to this area, which does not fit into the access opening.

By this means, the access opening of the adapter can be used to guide a drill, wherein the adapter can be partially set into the access opening of the drill guide, such that, in conjunction with the dental impression, the drill guide comprising the adapter forms a drilling template according to the invention for guiding a drilling tool.

Advantageously, the access opening of the drill guide or the drill guide adapter can be designed for a drilled implant hole or a pilot hole.

The diameter of the access opening of the drill guide itself or, in the case of a drill guide comprising an adapter, the access opening of the adapter, conforms to the diameter of the drill to be used, as is already generally known from the prior art for drill guides. Frequently, at least one initial hole with as small as possible a drilling diameter, referred to as a pilot hole, is drilled before the drilled implant hole, that is, a hole with a drilling diameter corresponding with the implant to be inserted. This is made possible by providing multiple drill guides, which can each be mounted on the dental impression arranged in the area of the implant site in the jaw. Multiple adapters with openings, each with different diameters, can also be provided, which can each be mounted on the drill guide arranged on the dental impression.

Advantageously, a stop for a drilling tool can be provided on one end of the drill guide facing away from the connecting part, wherein the drilling depth can be predefined by the length of the access opening.

In this case, a stop is referred to as a defined surface or edge of the drill guide, which works as a depth stop, that is, it prevents further penetration into the drill guide by a drill or drill insert of the drilling tool used. By this means, a drilling depth can be specified.

Advantageously, a longitudinal axis of the access opening of the drill guide can form an angle α with the longitudinal axis of the connecting part of the drill guide, which is preferably greater than 0° and less than or equal to 60°. By this means, it can be ensured that the access opening proceeds in the direction of a desired drilling direction.

In addition, the invention relates to a method for correlating an implant site in a jaw and a 3-D measurement dataset for the implant site. The method is designed to provide a dental impression showing a negative form of at least one partial area of a jaw on the underside and at least one implant site located in this partial area of the jaw, consisting of a radiolucent material and/or insulating material with at least one positioning aid that is at least partially radiopaque and/or partially visible in an MRI image. The positioning aid has a connecting part mounted on the dental impression, on an upper surface of the dental impression opposite the underside, in the area of the negative form of the implant site. At least one X-ray image and/or MRI image is taken, at least of the partial area of the jaw and of the at least one implant site located in this partial area, of the dental impression used at the implant site and of the at least one positioning aid mounted on the dental impression, and a 3-D measurement dataset from the at least one X-ray image and/or the at least one MRI image is generated. The location of the connecting part of the at least one positioning aid is determined relative to the implant site in the 3-D measurement dataset. By removing the positioning aid, a connecting part corresponding with the negative of the connecting part of the at least one positioning aid is prepared in a location consistent with the location of the connecting part of the positioning aid in the dental impression positionable at the implant site.

The correlation between the implant site to be treated in the patient's mouth and a 3-D dataset is provided for connecting further components by means of a connecting part, which is arranged in the mouth on a dental impression which can be positioned on the jaw and whose location in the 3-D dataset is known.

For this purpose, a positioning aid is mounted on a dental impression arranged on the implant site and measured on an X-ray image or an MRI image. The positioning aid is characterized by being at least partially radiopaque and hence visible on the X-ray image and/or in an MRI image, while the dental impression consisting of radiolucent and/or insulating material cannot be seen on the X-ray image and/or the MRI image. In addition, the implant site is visible on the X-ray image or the MRI image, such that the location of the radiopaque areas of the positioning aid or areas visible in the MRI image can be determined relative to the implant site from the X-ray image or the MRI image data.

The positioning aid has a connecting part, using which an area is defined, which is distinguished by a geometry enabling the positioning aid to be mounted on the upper surface of the dental impression. Here, for example, this can be an elevation, which can be mounted on the dental impression such that it is at least partially enclosed by the dental impression. For this purpose, the connecting part of the positioning aid designed as an elevation can, for example, be pressed into an impression compound applied at the implant site for creating the dental impression before it hardens and remain there while the impression compound is hardening. For this purpose, the connecting part is positioned as much as possible within the area of the implant site on the side of the impression compound corresponding with the upper surface of the dental impression.

It would also be possible to position a positioning aid designed as an elevation on the upper surface of the dental impression and to coat it with impression compound in such a way that it remains on the dental impression after this impression compound has hardened.

The connecting part of the positioning aid can also be designed as a recess, for example. This type of recess can, for example, be connected with the dental impression by being positioned on a suitable elevation on the dental impression. For this purpose, additional impression compound, for example, can be applied to the upper surface of the dental impression and the connecting part of the positioning aid can be imprinted on this additional impression compound, such that the additional impression compound at least partially fills the recess of the connecting part of the positioning aid.

The positioning aid is removed from the dental impression after the X-ray image has been taken, such that a negative form of the connecting part of the positioning aid remains at least partially on the dental impression. This region is in turn referred to as the connecting part of the dental impression, since it is suitable for attaching a further component having a connecting part corresponding with the positioning aid to the dental impression.

If the positioning aid has a connecting part designed as a rise, the connecting part of the dental impression is designed as a recess corresponding at least partially with the negative of this rise.

A further subject matter of the invention is a method for correlating an implant site of a jaw and a 3-D measurement dataset for the implant site, wherein an implant site on the underside having a negative form at least of a partial area of a jaw and at least of a dental impression positioned in this partial area of the jaw is prepared from a partially radiolucent material and/or from insulating material with at least one area which is radiopaque and/or visible in an MRI image, wherein the dental impression has a connecting part in the area of the negative form of the implant site on an upper surface of the dental impression opposite the underside and the relative location between the area which is radiopaque and/or visible in an MRI image and the connecting part is known. In addition, at least one X-ray image and/or MRI image at least of the partial area of the jaw, of the at least one implant site positioned in this partial area and of the dental impression positioned in the implant site is taken, and a 3-D measurement dataset is created from the at least one X-ray image and/or the at least one MRI image. The location of the area of the dental impression which is radiopaque and/or visible in an MRI image is determined relative to the implant site in the 3-D measurement dataset, and the relative location of the connecting part of the dental impression for the implant site is defined, based on the relative location of the area which is radiopaque and/or visible in an MRI image.

As in the method described above, this method according to the invention creates a correlation between an implant site in the patient's mouth and a 3-D dataset. The connecting part arranged on the dental impression, whose position in the 3-D dataset is known, can be used as an orientation aid for transferring locations and directions from the 3-D dataset into the physical space in the patient's mouth.

For this purpose, an X-ray image and/or MRI image of a dental impression arranged in the implant site is created in this further method according to the invention. The dental impression has a connecting part, that is, an area suitable for attaching a further component onto the dental impression. In addition, the dental impression consists of as great a proportion as possible of a radiolucent material not discernible in an X-ray image and/or an insulating material not visible in an MRI image. Only a smaller area should consist of material which is radiopaque and hence visible in an X-ray image and/or a material discernible in an MRI image, for example, a conductive material. The position of this area of the dental impression for the connecting part which is radiopaque and/or discernible in an MRI image is known. Thus, on the one hand, as few areas as possible of the jaw and of the implant site in the X-ray image or the MRI image are obscured by the dental impression while, on the other hand, the relative location of the connecting part of the dental impression for the implant site can be determined.

A further subject matter of the invention is a method for correlating an implant site in a jaw and a 3-D measurement dataset for the implant site, wherein a dental impression is provided, positioned in this partial area of the jaw featuring a negative form of at least a partial area of a jaw on the underside and at least one implant site, consisting of a radiolucent material and/or insulating material. In addition, at least one visual positioning aid is provided, which has a connecting part passing through the dental impression from an upper surface of the dental impression opposite the underside in the area of the negative form of the implant site on the dental impression and extending past the underside of the dental impression, and which has at least one fixed or detachably arranged locator on the end projecting past the underside of the dental impression. At least one X-ray image and/or MRI image is taken, at least of the partial area of the jaw and of the at least one implant site located in this partial area, and a 3-D measurement dataset is generated from the at least one X-ray image and/or the at least one MRI image. In addition, at least one visual image is taken of the underside of the dental impression, with the visual positioning aid inserted and projecting past the underside of the dental impression with the at least one locator inserted on the projecting connecting part on the positioning aid, and a further 3-D measurement dataset is created from the at least one visual image. A correlation measurement dataset is generated from the 3-D measurement datasets created by correlation, and the location of the connecting part of the at least one visual positioning aid relative to the implant site is determined in the correlation dataset. By removing the visual positioning aid, a connecting part corresponding with the negative of the connecting part of the at least one visual positioning aid is prepared in a location consistent with the location of the connecting part of the visual positioning aid in the dental impression positioned on the implant site determined in the correlation dataset.

As in the method described above, this method according to the invention creates a correlation between an implant site in the patient's mouth and a measurement dataset. For this purpose, an X-ray image and/or an MRI image of a dental impression arranged on the implant site and a visual image of an underside of the dental impression are correlated in this further method according to the invention.

The X-ray image and/or MRI image of the region of the jaw is taken, which comprises the implant site and whose negative form is impressed on the underside of the dental impression to be measured visually.

A visual positioning aid is mounted on the dental impression for the visual image, which has a connecting part extending from the upper surface of the dental impression through the dental impression, such that it projects past the underside of the dental impression. At least one locator is arranged on the end projecting past the underside while the visual image is being produced.

A locator is characterized by having a particular external shape that is easily recognizable in a visual image, such that the exact position of the locator relative to the imaged surface of the underside of the dental impression in the visual image can be determined in the visual image. Thus, the position of the connecting part of the visual positioning aid in the visual image can be deduced from the known location of the locator relative to the connecting part of the visual positioning aid, even if this is partially located in the dental impression and is itself, therefore, not discernible in the visual image.

The correlation dataset can be generated in accordance with a method known from the prior art for correlating radiological and visual data, for example, the method described in DE 199 52 962 A1.

A correlation between the known location of the connecting part of the visual positioning aid in view of the visual image and the X-ray image is produced by means of this correlation. Hence, it is possible to determine all points or locations in the X-ray image, for example, a drilling direction or drilling depth for a drilled implant hole determined in the X-ray image, a corresponding location relative to the connecting part of the visual positioning aid arranged on the dental impression or, after removing the visual positioning aid, relative to the connecting part of the dental impression.

A further subject matter of the invention is a method for creating a drilling template for a hole to be drilled at an implant site, for which an implant site is provided on the underside of a negative form of at least one partial area of a jaw and having at least one dental impression located in this partial area of the jaw, with at least one connecting part of known connection geometry, wherein the connecting part in the area of the negative form of the implant site is arranged on an upper surface of the dental impression opposite the underside, and whose location relative to the jaw where a dental impression is positioned at the implant site is known. In addition, a drilling direction relative to the connecting part of the dental impression is determined for at least one implant by reference to a 3-D measurement dataset for the jaw including the implant site, and at least one drill guide is produced with a connecting part consisting of a block with an access opening proceeding along a longitudinal axis of the block, wherein the connecting part corresponds at least partially to the negative of the connecting part of the dental impression, and wherein the connecting part is arranged at an angle to the access opening, which corresponds with an angle of the drilling direction to the connecting part of the dental impression. The at least one drill guide is mounted on the dental impression, wherein a correct orientation of the drill guide on the dental impression is ensured by means of the connecting parts.

A drilling template according to the invention is created from an impression and a drill guide.

For this purpose, the dental impression has an underside with a negative form of a partial area of a jaw, wherein the partial area comprises at least one implant site. In addition, the dental impression has a connecting part, which is arranged on an upper surface opposite the underside of the dental impression in the area of the implant site. The connecting part is an area of the dental impression that has a known geometry, which is suitable for mounting a further component. This may be a recess, for example, into which a further component can be at least partially inserted. The connecting part may also be designed as an elevation, onto which a further component can be attached. In addition, the position of the connecting part relative to the jaw is known.

The parameters for the implant drilling, in particular the drilling direction as well as the drilling diameter and/or drilling direction and the drilling depth, are determined in a 3-D measurement dataset, which includes the implant site. By means of the known relative location between the implant site and the connecting part of the dental impression, these dimensions are determined relative to the connecting part of the dental impression.

By reference to these parameters, a drill guide is produced by arranging a connecting part on a block, wherein the block already has an opening proceeding along a longitudinal axis. The connecting part to be produced is characterized in that it is arranged along the longitudinal axis of the block at one end of the block and at an angle to the longitudinal axis of the block with respect to a longitudinal axis of the connecting part. The connecting part is shaped in such a way that it corresponds at least partially with the negative of the connecting part of the dental impression, such that the drill guide can be mounted on the dental impression by connecting the connecting parts. This connection can be achieved by at least partial interlocking. This can, for example, be a plug connection.

If the block is clamped in a bracket while the connecting part is being produced, it is detached therefrom after completing the production along a plane that is angled relative to the opening, such that a component with a connection geometry and an opening is provided as a drill guide.

The angle between the connecting part of the drill guide to be produced and the opening of the block used for the drill guide is selected in such a way that it corresponds with the angle of the determined drilling direction to the connecting part of the dental impression. Thus, after introducing the drill guide into the dental impression, the access opening of the drill guide proceeds in accordance with the predefined drilling direction.

The directional course and the location of the plane on which the block is separated by a bracket or of the end of the block facing away from the connecting part can determine the drilling depth, for example, by a stop on the drill to be used, or may at least represent one control option. It is possible, for example, to provide a depth stop or end stop for a drilling tool by means of the surface or edge resulting after the separation or by means of the terminating surface of the block, which prevents further penetration by the drill and therefore defines a maximum drilling depth.

Advantageously, a drilling diameter relative to the connecting part of the dental impression is also determined in addition to the drilling direction for at least one implant, and a block with a cylindrical opening with a diameter in accordance with a determined drilling diameter is used.

The diameter of the opening of the block to be used can be selected such that this, as has already been explained for drilling templates, corresponds with the desired drilling diameter in a suitable manner, in order to ensure reliable guidance for a drill in the drilling template.

Advantageously, a drilling diameter relative to the connecting part of the dental impression is determined for at least one implant, and a block with an opening with a diameter which is larger than the determined drilling diameter is used for producing the drill guide, wherein the drill guide is used together with an adapter, which has an area with an external geometry corresponding with the negative of the opening of the block, a terminal area connecting to this area, and an access opening with an internal diameter determined in accordance with the drilling diameter, and on which the side of the drill guide produced from the block facing away from the connecting part of the drill guide is at least partially introduced into the access opening of the drill guide.

Producing the drill guide from a block with a diameter greater than the drilling diameter enables adapters to be provided, which are suitable for reducing this diameter to the desired size. For this purpose, the adapter has an access opening of the desired diameter, for example, the drilling diameter or a diameter suitable for a pilot hole, and an external form, which enables the adapter to be inserted at least partially into the access opening of the drill guide such that the access opening of the adapter proceeds parallel to the access opening of the drill guide and partially within the access opening of the drill guide. By this means, a drilling template is provided, consisting of a dental impression and a drill guide with an adapter of a desired drilling diameter. By providing multiple adapters of various access opening diameters, it is also possible, to provide a drilling template, which can be used for an initial pilot hole, as well as for further drilling or for the implant drilling, by simple means, namely, by exchanging the adapter.

Advantageously, at least the connecting part of the drill guide is milled or ground from the block. This is as simple a production variant as possible, which is enabled in particular by using blocks with a predrilled opening and by arranging the connection geometry at an angle.

Advantageously, the block is clamped in a bracket at least during the production of the connecting part and is detached from the bracket along a separation plane perpendicular or at an angle to the longitudinal axis of the block prior to insertion.

The directional course and the location of the plane on which the block is separated by a bracket, in which this is clamped while the connection geometry is produced, can correspond with a determined drilling depth. Hence, it is possible to provide a depth stop or end stop for a drilling tool by means of the surface or edge resulting after the separation, which prevents further penetration by the drill and therefore defines a maximum drilling depth.

EMBODIMENTS

Figure 1:
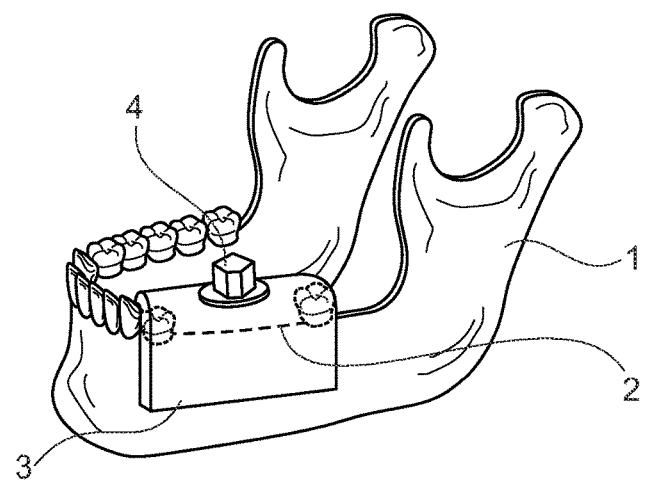
FIG. 1 a dental impression according to the invention for an implant site and a section of an adjacent jaw with a positioning aid, FIG. 2 the positioning aid from FIG. 1, FIG. 3 the dental impression from FIG. 1, FIG. 4 a drill guide for a drilling template according to the invention.

FIG. 1 shows a part of a jaw 1, here, by way of example, a mandible, comprising an implant site 2, that is, a site in the jaw 1 or an area of the jaw 1, in which an implant is to be placed in the jaw 1. The shown implant site 2 is located in an edentulous space in the mandible 1, in the area of which at least one drilled implant hole is to be placed for at least one implant. Here, an edentulous space is understood to mean a tooth gap bordered by other teeth. It could also be an implant site 2 on the maxilla 1 or one of several implant sites 2 in a completely edentulous jaw 1 or a free-end gap, that is, a tooth gap that only has adjoining teeth on one side.

A dental impression 3 is formed from an impression compound that is radiolucent and/or insulating, at least when solidified, mounted in the area of the jaw 1 comprising the implant site 2. The impression compound may be rapid-curing, for example. It is essential that the impression compound in its solidified form, that is, as a dental impression 3, does not further deform or, alternately, returns elastically to the original shape when deformed from its initial shape.

Another essential characteristic is that the dental impression is not discernible in an X-ray image or in an MRI image. For this purpose, the impression compound is radiolucent, at least when solidified, or consists of an insulating material. As a rule, insulating materials such as polyethylene, polyurethane, polymers or fiberglass are not visible in an MRI image.

The dental impression 3 has an underside 3" with a negative form of the area of the jaw 1 comprising the implant site 2 and an upper surface 3' opposite the underside 3". The adjacent teeth serve as orientation or for positioning the dental impression on the implant site 2.

Prior to the hardening of the impression compound, a positioning aid 4 is introduced at least partially into the impression compound or is mounted on the impression compound in the area of the proposed implant, on the side of the dental impression facing away from the mandible 1 or the implant site 2, that is, on the upper surface 3' of the dental impression 3. This can be accomplished, for example, by being subsequently pressed into the already introduced but not yet hardened impression compound or by being mounted and subsequently overmolded or kneaded with additional impression compound.

If multiple implants are to be inserted, a positioning aid 4 is at least partially inserted into the impression compound or mounted on the impression compound for each of these proposed implants in the area in the proposed location. The procedure in respect of each individual proposed implant is as described here by way of example for one proposed implant.

Figure 2:
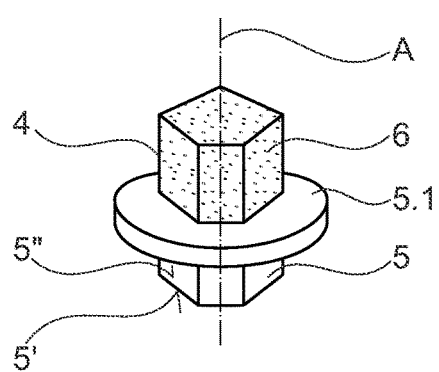

The positioning aid 4, which is shown in detail in FIG. 2, has at least one area 6, which is radiopaque or not discernible in an MRI image, as well as one connecting part 5 for mounting on the dental impression 3. The positioning aid may partly consist of, for example, a material discernible in an MRI image, for example, an electrically conductive material such as a metal.

Connecting part 5 means an area of the positioning aid 4, which, due to its geometry, is suitable for mounting the positioning aid on the dental impression 3. This geometry of the connecting part 5 is known. Additionally, the location of the connecting part 5 of the positioning aid 4 relative to the area 6 of the positioning aid 4 which is radiopaque and/or visible in an MRI image and the geometry of the radiopaque area itself is also known.

The area 6 which is radiopaque and/or visible in an MRI image is a freely designed and arranged area of the positioning aid 4, which is characterized in that it is radiopaque, that is, discernible in an X-ray image. The area 6 may, for example, consist of multiple, e.g. three, spheres made from material which is radiopaque and/or discernible in an MRI image, which spheres are arranged next to one another on the connecting part 5 of the positioning aid 4 or on an area of the positioning aid 4 attached to the connecting part 5. The area 6 may also extend beyond the connecting part 5. It would be possible, for example, for the area 6 which is radiopaque and/or visible in an MRI image to extend beyond the entire positioning aid 4, thus making this entirely radiopaque or visible in an MRI image.

In the embodiment shown in FIG. 2, the connecting part 5 is designed as a rise with a longitudinal axis A proceeding in the direction of the rise. The rise has multiple side panels 5" parallel to the longitudinal axis, which together form a five-sided cross-section and which terminate in a flat base 5' perpendicular to the longitudinal axis A of the connecting part 5. The longitudinal axis A corresponds with the direction of connection of the positioning aid 4, that is, the direction of insertion or attachment, along which the connecting part 5 of the positioning aid 4 is introduced into the dental impression 3. The sides of the five-sided cross-section are of different lengths, such that the connecting part 5 designed as a rise has a geometry with precise angles relative to the longitudinal axis A. If the positioning aid is removed from the dental impression and is inserted again, the precisely angled geometry prevents a rotated insertion.

The connecting part 5 of the positioning aid 4 could also, for example, be designed as a recess with a longitudinal axis in the direction of the depression. The connecting part 5 could also have only one single side panel 5", which, for example, is oval in cross-section. The side panels can also be set at an angle relative to the longitudinal axis of the connecting part 5. It is only essential that the geometry of the connecting part has an area with a precisely angled geometry relative to its longitudinal axis A. Hence, the connecting part could be designed, for example, as a mold with an oval cross-section. The cross-section could also, for example, taper off in the direction of the rest of the positioning aid 4, whereby it can be removed more easily from the dental impression.

The positioning aid 4 shown in FIG. 2 has a radiopaque area 6, shown as a dotted area, which is designed as a radiopaque rise with a geometry similar to the connecting part 5.

The positioning aid 4 shown in FIG. 2 moreover has a plate-shaped area 5.1 arranged between the connecting part 5 and the area 6 which is radiopaque and/or visible in an MRI image. The plate-shaped area 5.1, terminating the connecting part, can serve as a support surface on the upper surface 3' of the dental impression 3 and hence as a type of end stop for the insertion depth of the positioning aid 4 when the positioning aid 4 is inserted into the dental impression 3. A positioning aid 4 according to the invention does not have to have this type of plate-shaped area 5.1.

The positioning aid 4 can be designed as a single piece, as in the case shown. The positioning aid 4 can also be designed in multiple pieces. It is possible, for example, to design the positioning aid 4 from two connectable components, wherein one component comprises the connecting part 5 and the other component, for example, has at least one area 6 which is radiopaque and/or visible in an MRI image. By this means, for example, it would be possible to position only the part comprising the connecting part 5 in the impression compound for the dental impression 3 in the patient's mouth and to leave this in the patient's mouth while the impression compound sets. For example, because this first part by itself does not project as far past the upper surface 3' of the impression compound or the dental impression 3, it prevents that the positioned part of the positioning aid 4 is moved by the patient's tongue before the impression compound has set.

By attaching the connecting part 5 of the positioning aid 4 to the not yet solidified impression compound by inserting or mounting this on the upper surface 3' of the dental impression 3 and then removing the positioning aid 4 after the dental impression 3 has hardened, a connecting part 7 is created in the dental impression 3, on the upper surface, which corresponds with the negative of the connecting part 5 of the positioning aid 4.

Figure 3:
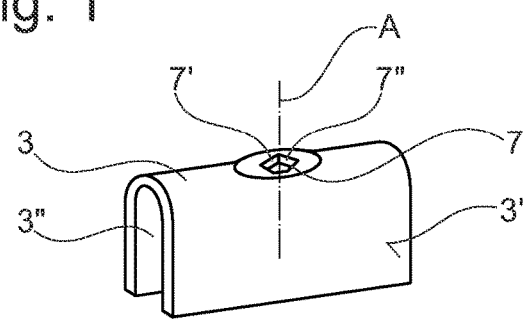
Figure 12:
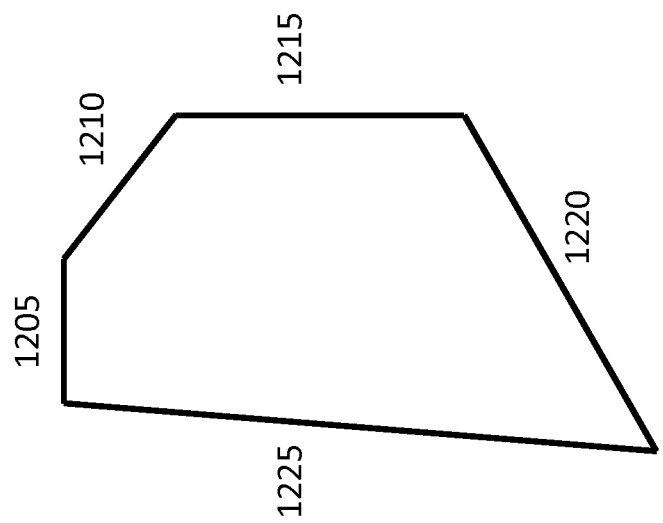
FIG. 12 is a cross-sectional profile of a recess according to the invention.
Figure 13:
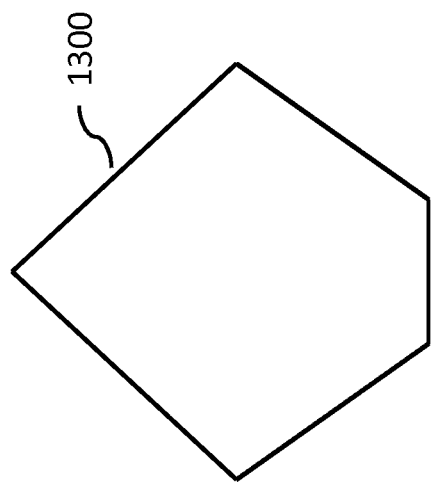
FIG. 13 is a cross-section profile of a rotationally asymmetric recess according to the invention.

In the embodiment shown, a connecting part 7 is formed, as shown in FIG. 3, as a recess relative to the upper surface 3' of the dental impression with a longitudinal axis A proceeding in the direction of the recess, a base 7' and a geometry with precise angles relative to the longitudinal axis A. By this means, introducing a component fitting into the connecting part 7 of the dental impression 3 at a precise angle is guaranteed. FIG. 12 is a cross-sectional profile of a recess whose sides 1205, 1210, 1215, 1220, and 1225 are of different lengths. FIG. 13 is a cross-section profile of a rotationally asymmetric recess 1300, as shown in FIG. 3.

It is also possible for the connecting part 5 of the positioning aid 4 to completely break through the dental impression 3 in the direction of the longitudinal axis A of the connecting part 7 formed in the dental impression 3, such that the connecting part 7 of the dental impression 3 lacks a base 7'.

If the connecting part 5 of the positioning aid is designed as a recess, a connection geometry 7 on the upper surface 3' of the dental impression 3, designed as a negative of this connection geometry 5, for example, can be formed by applying excess impression compound to the upper surface 3' of the dental impression 3 and the connection geometry 7 is formed by positioning the connection geometry 5 of the positioning aid 4. The connecting part 7 formed as a rise then has a cap rather than a base.

The dental impression 3 positioned on the implant site 2 with the connecting part 7 with a known geometry serves as an orientation aid by creating a correlation between the implant site 2 on the jaw 1 and a 3-D measurement dataset 21 for the implant site 2. For this purpose, at least one X-ray image and/or MRI image is taken of the implant site 2 with the dental impression 3 positioned there and the positioning aid 4 mounted thereto.

Figure 9:
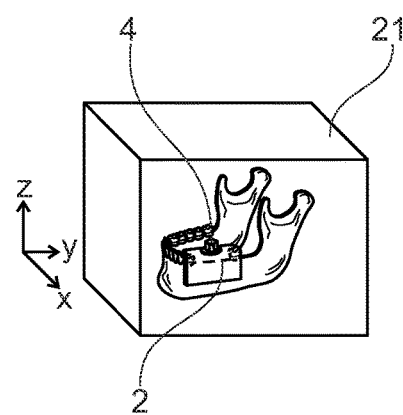

The dental impression 3 is not discernible in the at least one 3-D dataset 21 determined in the at least one X-ray image and/or MRI image. Both the implant site 2 and the at least one region 6 of the positioning aid 4 which is radiopaque or visible in an MRI image are discernible in the 3-D dataset 21, as shown schematically in FIG. 9. The location of the connecting part 5 of the positioning aid 4 relative to the implant site 2 discernible in the 3-D dataset is determined on the basis of the known relative location between the at least one area 6 of the positioning aid 4 which is radiopaque and/or visible in an X-ray image and the connecting part 5 of the positioning aid 4. Since the position of the connecting part 5 of the positioning aid 4 mounted on the dental impression 3 conforms with the position of the connecting part 7 of the dental impression 3, the location of the connecting part 7 of the dental impression 3 relative to the implant site 2 is therefore also known. Hence, by means of its connecting part 7, the dental impression 3 positioned on the implant site 2 creates an orientation aid after the positioning aid 4 is removed, which produces a correlation between the implant site 2 on the mandible 1 and the at least one 3-D measurement dataset 21.

By this means, a course for a proposed drilled implant hole, hereafter referred to as a drilling direction, can be determined in the 3-D dataset 21 and, subsequently, the location of the drilling direction relative to the connecting part 7 of the dental impression 3 positioned on the mandible 1 can be ascertained. In particular, an angle between the longitudinal axis A of the connecting part 7 of the dental impression 3 and the drilling direction can be determined, as well as an angular orientation for the drilling direction relative to the longitudinal axis A of the connecting part 7 of the dental impression 3.

Figure 4:
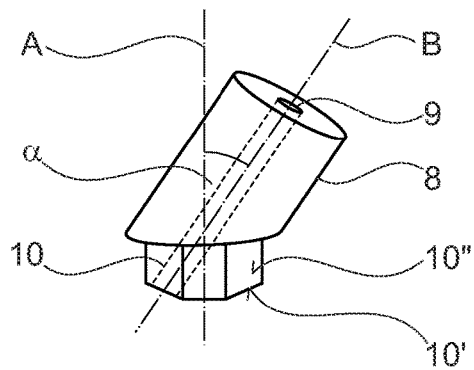

Based on this knowledge, a drill guide 8 according to the invention can be produced, as shown in FIG. 4. The drill guide 8 according to the invention has an access opening 9 and a connecting part 10 for connection with the dental impression 3. The connecting part 10 of the drill guide 8 shown in FIG. 4 is formed for this purpose as a negative form of the connecting part 7 of the dental impression 3 and hence has a rise and a longitudinal axis A proceeding in the direction of the rise.

The connecting part 10 of the drill guide 8 can also be designed only partially as a negative form of the connecting part 7 of the dental impression 3, wherein it should be ensured that the connecting part 10 of the drill guide 8 fits the connecting part 7 of the dental impression with precise angles relative to the longitudinal axis A and that the drill guide can be snugly connected with the dental impression. Only by means of a snug connection and by preventing a rotated insertion can it be guaranteed that the access opening 9 of the drill guide will proceed in the drilling direction relative to the jaw defined in the 3-D dataset when introduced into the dental impression positioned on the jaw.

The access opening 9 is designed as a cylindrical opening with a longitudinal axis B following the course of the opening and whose course is shown in FIG. 4 by a dashed line. The access opening 9 is aligned with the connecting part 10 of the drill guide 8, in such a way that the longitudinal axis B of the access opening 9 forms an angle α with the longitudinal axis A of the connecting part 10 of the drill guide 8, which corresponds with the angle determined between the proposed drilling direction and the connecting part 7 of the dental impression 3. Additionally, the longitudinal axis B is oriented at an angle in relation to the longitudinal axis A of the connecting part 10 of the drill guide 8, as was determined for the proposed drilling direction in relation to the longitudinal axis of the connecting part 7 of the dental impression 3.

If the connecting part 10 of the drill guide 8 is introduced into the connecting part 7 of the dental impression 3 or attached to the connecting part 7 of the dental impression 3 in such a way that the longitudinal axis A of the connecting part 10 of the drill guide 8 coincides with the longitudinal axis A of the connecting part 7 of the dental impression 3, a corresponding angle α results between the longitudinal axis A of the connecting part 7 of the dental impression 3 and the longitudinal axis B corresponding with the course of the access opening 9 and an angled orientation of the access opening 9 relative to the longitudinal axis A of the connecting part 7 of the dental impression 3, such that the access opening 9 proceeds along the drilling direction determined beforehand.

Figure 5:
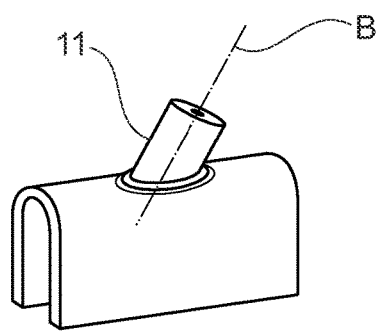
FIG. 5 an adapter.

The access opening 9 serves as a guide for a drill and hence specifies a direction for the drilled hole relative to the connecting part 7 of the dental impression 3 introduced into the dental impression 3 for the drill guide 8. Together, the dental impression 3 and the applied drill guide 8 form a drilling template 11 according to the invention, which is shown in FIG. 5.

As shown in FIG. 4, the access opening 9 of the drill guide 8 can have a cylindrical geometry, whose diameter is determined by the diameter of the drill to be used for the drilled implant hole, to the effect that the drill can be reliably guided during the implant drilling.

Figure 6:
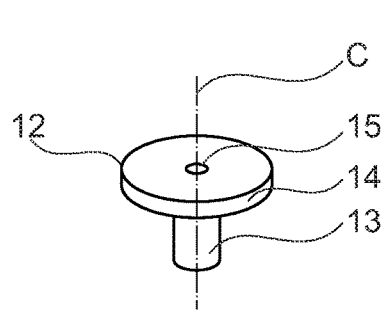
FIG. 6 a schematic representation of the production of a drill guide from a block, FIG. 7 another variant of a drill guide to be produced from a block, FIG. 8 a drilling template according to the invention, FIG. 9 a 3D data set of the implant site and one region of the positioning aid, FIG. 10 a visual positioning aid according to the invention, FIG. 11 a measurement dataset obtained from a visual measurement.

The drill guide 9 can comprise an adapter 12, as shown in FIG. 6. For this purpose, the access opening 9 can have a cylindrical cross-section, into which one or more adapters 12 can be introduced. For this purpose, this type of adapter 12 according to the invention has an external geometry with an elongated end 13 which fits into the access opening 9 of the drill guide 8 and this end terminates in a plate 14. The plate 14 has a diameter, which is larger than the corresponding diameter of the end 13, in a plane perpendicular to a longitudinal axis C of the end 13, which fits into the access opening 9 of the drill guide 8. By this means, a maximum penetration depth of the adapter 12 is realized when elongated end 13 is introduced into the access opening 9 of the drill guide 8. In addition, the adapter 12 has an access opening 15, which proceeds along the longitudinal axis C and which has a diameter that corresponds with the drilling diameter of a proposed drilled hole.

Hence, for example, multiple adapters 12 of various diameters can be provided for the access opening 15 in order to create a pilot hole, for example, with the aid of a first adapter 12 and, subsequently, a drilled implant hole by means of a further adapter 12.

If a drill guide 8 comprising at least one adapter 12 is used, the cross-section of the access opening 9 of the drill guide 8 can take any form, wherein the at least one adapter 12 has an end 13 with a corresponding external geometry. The access opening 9 of the drill guide 8 may have, for example, a square cross-section and the adapter 12 may have an end 13 with a corresponding square external geometry.

Figure 7:
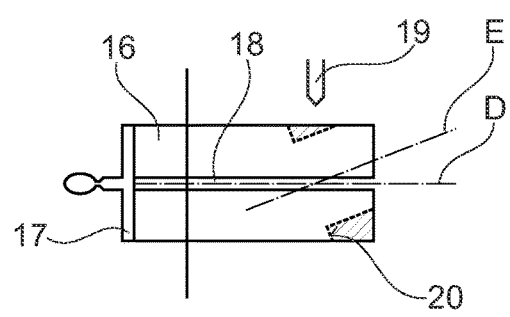
Figure 8:
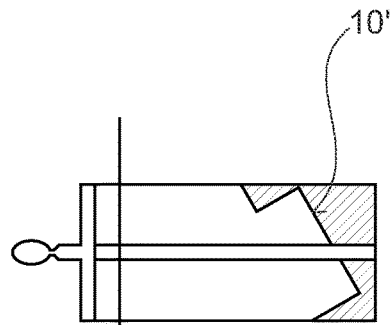

The production of the drill guide 8 according to the invention for a drilling template 11 made from a block 16 is shown schematically in FIGS. 7 and 8. The block 16 clamped on a bracket 17 has an opening 18 along a longitudinal axis D of the block 16, corresponding with the access opening 9 of the drill guide 8 to be produced. The connecting part 10 of the drill guide 8 to be produced is made by an ablative process using a grinding or milling tool 19 on an end of the block which is facing away from the bracket 17, by forming the side panels 10" of the connecting part 10 flat and parallel to an axis E, wherein the axis E is aligned to the longitudinal axis D of the opening 18 of the block 16 in such a way that the proposed drilling direction proceeds along the longitudinal axis A of the connecting part 7 of the dental impression 3.

In addition, support surfaces 20 are designed in the junction between the connecting part 10 and a clamp end of the block 16, which can be used to position the drill guide 8 on the upper surface 3' of the dental impression 3 in the area around the connecting part 7.

The support surfaces 20 can be designed relative to the longitudinal axis of the connecting part 10. They can also form an angle with the longitudinal axis. It is essential that they ensure a defined depth stop. A depth stop can be ensured, for example, by the junction between the connecting part 10 and the support surface 20, for example, by the edge formed at the junction that can be attached in an interlocking fashion on the shoulder formed at the junction of the side panels 7" of the connecting part 7 of the dental impression 3 and the upper surface 3' of the dental impression 3.

The variant shown in FIG. 7 provides that the connecting part 10 of the drill guide 8 to be produced is supported by means of the support surfaces 20 on the upper surface 3 of the dental impression 3', wherein the connecting part 10 of the drill guide is guided between the lateral surfaces 7" of the connecting part 7 of the dental impression 3, without the connecting part 10 of the drill guide 8 coming into contact with the base 7' of the connecting part 7. In this kind of case, only the side panels 10" proceeding parallel to the axis E and the support surfaces 20 must be milled from the block.

The variant shown in FIG. 8 provides that the connecting part 10 of the drill guide 8 to be produced, when mounting the dental impression 3, makes contact both with the support surface 20 on the upper surface 3' of the dental impression 3 and with the base 10' on the base 7' of the connecting part 7 of the dental impression 3. In addition to the side panels 10" and the support surfaces 20, in this case, the base 10' of the connecting part must also be produced by corresponding machining of the block.

Additionally, it would also be possible to shape the connecting part 10 of the drill guide 8 in such a way that this comes into contact with the base 7' and the side panels 7" of the connecting part 7 of the dental impression without, however, the support surfaces 20 resting on the upper surface of the dental impression.

If the connecting part 10 of the drill guide 4 is entirely produced, the block bracket 17 and, optionally, a part of the end of the block 16 on the bracket side are separated along a plane F, perpendicular to the opening 18 or the longitudinal axis D of the block 16. The drill guide 8 can now be attached to the dental impression 3, in order to form the drilling template 11 according to the invention therewith.

In addition to the drilling direction, the drilling depth can also be controlled or determined by means of the drilling template 11 according to the invention. For this purpose, a drilling depth relative to the jaw 1 for the drilled implant hole is also stipulated in the 3-D dataset 21, in addition to the drilling direction. Hence, a location corresponding with the drilling direction, relative to the connecting part 7 of the dental impression 3 can be determined for the end position of the proposed drilled implant hole arising therefrom.

This location can be determined, for example, relative to the base 7' of the connecting part 7 of the dental impression 3 or relative to an adjacent edge or shoulder of the connecting part 7 on the upper surface 3' of the dental impression 3. Thus, the penetration depth of a drill to be used can be limited by the length of the access opening 9 of the drill guide 8. The length can be measured or specified from the base 10' of the connecting part 10 of the drill guide 8 or from the support surfaces 20 of the connecting part 10 of the drill guide 8 or from the edge forming at the junction between the side panels 10" of the connecting part 10 and the support surface 20 of the drill guide 8 to the end of the drill guide facing away from the connection geometry. It is essential that the support point or the support surface of the drill guide 8 of the dental impression 3 is known.

Hence, the drilling depth for a drill with a suitable end stop on the drill itself can be regulated by the drilling template according to the invention by means of the length of the access opening 9 of the drill guide. For example, a shoulder firmly fixed on the drill at a fixed length relative to the drill end can serve as an end stop, wherein the drill can penetrate into the access opening 9 of the drill guide 8 until the shoulder rests at least partially on the side of the drill guide 8 facing away from the connection geometry.

If a drill without an end stop is used, the penetration depth of the drill can be determined by reading a value on the drill used at the height of the side of the geometry of the drill guide 8 facing away from the connection because the length of the access opening 9 of the drill guide 8 relative to the connecting part 7 of the dental impression 3 is known.

Instead of a positioning aid 4 which is radiopaque and/or discernible in an MRI image, a visual positioning aid 22 can also be used in order to create a correlation between an implant site and a 3-D dataset by means of a dental impression 3 according to the invention with a connecting part 7, and a visual measurement can be made in addition to an X-ray image and/or an MRI image.

Figure 10:
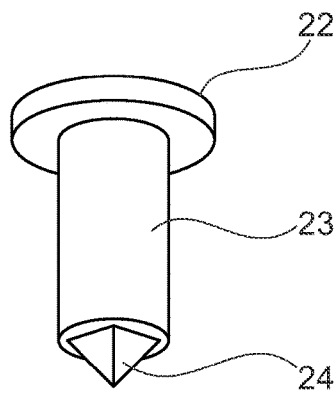

A visual positioning aid 22, which is shown by way of example in FIG. 10, has a connecting part 23, as does the previously described positioning aid 4, whose negative form is reflected in or on the dental impression. In addition, the visual positioning aid 22 is designed in such a way that it completely passes through the dental impression 3, i.e. that the visual positioning aid 22 penetrates the dental impression 3 through the upper surface 3' and also breaks through the underside 3" of the dental impression 3 opposite the upper surface 3', such that a part of the visual positioning aid 22 projects past the underside 3" of the dental impression 3.

At least one locator 24 is arranged on the end of the visual positioning aid 22 emerging from the underside 3", which is characterized by a specific geometry with distinct surfaces, by means of which the precise location of the locator 24 can be determined in a visual image. A locator 24 can be designed as a tetrahedron, for example. The locator 24 can be mounted on the positioning aid 22 in such a way that the relative location of the locator 24 or of the individual surfaces of the locator 24 for the connection geometry 23 of the positioning aid 22 is known.

Figure 11:
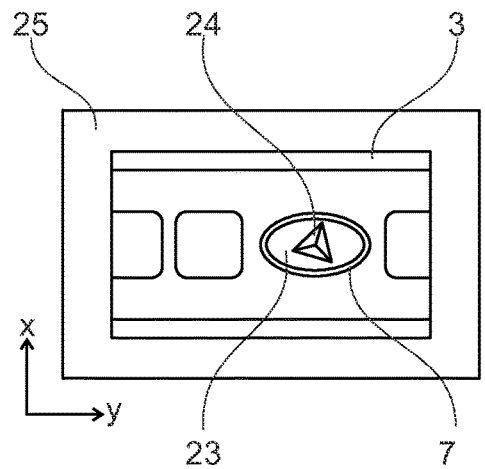

The underside 3' of the dental impression 3 with the positioning aid 22 and the locator 24 are measured visually, and a 3-D dataset 25 is created from the visual image, as shown by way of example in FIG. 11.

This 3-D dataset 25 is correlated with the 3-D dataset created from the X-ray image or from the MRI image, for example, by reference to tooth surfaces that can be discerned in both measurement datasets. The relative location of the locator 22 for the implant site 2 can be determined in the correlation dataset 25 created here, and the location of the connecting part 23 of the visual positioning aid can be derived therefrom, whereby, in turn, the location of the connecting part 7 of the dental impression is known.

The invention claimed is:

1. A dental positioning apparatus, comprising: a dental impression that includes:
    an underside having a negative form of at least one partial area of a jaw and at least one implant site located in the partial area of the jaw, and
    a connecting part comprising a recess formed in an upper surface of the dental impression, opposite the underside, in an area of the negative form of the implant site, wherein the connecting part has a longitudinal axis defined along a depth direction of the recess, and wherein a cross-sectional profile of the recess in a plane perpendicular to the longitudinal axis is rotationally asymmetric about the longitudinal axis,
    wherein the dental impression is formed from an impression compound capable of a first physical state, where the impression compound is a malleable solid, and a second physical state, where the impression compound is a non-malleable solid; and
a positioning aid component that comprises a positioning aid component connecting part
    wherein a cross-sectional profile of the positioning aid component connecting part, in the plane perpendicular to the longitudinal axis, corresponds to the cross-sectional profile of the recess, and
    wherein a portion of the positioning aid component protrudes from the recess formed in the upper surface of the dental impression when inserted in the recess; and
a drill guide that includes a drill guide connecting part, wherein a cross-sectional profile of the drill guide connecting part, in the plane perpendicular to the longitudinal axis, corresponds to the cross-sectional profile of the recess,
    wherein an entire outer periphery of the positioning aid component connecting part is dimensioned to fit within the recess formed in the upper surface of the dental impression, and
wherein an entire outer periphery of the drill guide connecting part is dimensioned to fit within the recess formed in the upper surface of the dental impression.

2. The dental positioning apparatus according to claim 1, wherein the connecting part and the underside are unibodily formed.

3. The dental positioning apparatus according to claim 1, wherein the dental impression includes a base of the recess such that the recess does not continue to the underside of the dental impression.

4. The dental positioning apparatus according to claim 1, wherein the positioning aid component includes a radiopaque material.

5. The dental positioning apparatus according to claim 1, wherein the recess has at least one side panel adjacent to the upper surface of the dental impression.

6. The dental positioning apparatus according to claim 1, wherein the recess is defined by a plurality of sides of different lengths.

7. The dental positioning apparatus according to claim 1, wherein the positioning aid component connecting part includes a plurality of side panels of different lengths.

8. The dental positioning apparatus according to claim 1, wherein the positioning aid component includes a radiopaque material disposed outside of and above the recess in the longitudinal direction.

9. The dental positioning apparatus according to claim 1, wherein the positioning aid component includes a support portion, and
    wherein a surface of the support portion contacts the upper surface of the dental impression.

10. The dental positioning apparatus according to claim 1, wherein the dental impression is radiolucent in the second physical state.

11. The dental positioning apparatus according to claim 1, wherein the impression compound includes an insulating material.

12. The dental positioning apparatus according to claim 11, wherein the insulating material is one of: polyethylene, polyurethane, or fiberglass.

13. The dental positioning apparatus according to claim 11, wherein the insulating material is a polymer.

14. The dental positioning apparatus according to claim 1, wherein the positioning aid component does not include a drill guide hole.

15. The dental positioning apparatus according to claim 1, wherein the impression compound is not an acrylic resin.

* * * * *